(12) United States Patent  
Anderson et al.

(10) Patent No.: US 8,590,529 B2
(45) Date of Patent: Nov. 26, 2013

(54) ACTUATOR FOR AN INHALER

(75) Inventors: Gregor John McLennan Anderson, Ware (GB); Penelope Ann Burgess, Ware (GB); Gary Thomas Crosby, Ware (GB); Tristan Fairbrother, Ware (GB); Philip William Farr, Ware (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 709 days.

(21) Appl. No.: 12/377,403

(22) PCT Filed: Aug. 21, 2007

(86) PCT No.: PCT/EP2007/058678
§ 371 (c)(1),
(2), (4) Date: Feb. 13, 2009

(87) PCT Pub. No.: WO2008/023018
PCT Pub. Date: Feb. 28, 2008

(65) Prior Publication Data
US 2010/0224185 A1    Sep. 9, 2010

Related U.S. Application Data

(60) Provisional application No. 60/823,134, filed on Aug. 22, 2006, provisional application No. 60/823,139, filed on Aug. 22, 2006, provisional application No. 60/823,141, filed on Aug. 22, 2006, provisional application No. 60/823,143, filed on Aug. 22, 2006, provisional application No. 60/823,146, filed on Aug. 22, 2006, provisional application No. 60/823,151, filed on Aug. 22, 2006, provisional application No. 60/823,154, filed on Aug. 22, 2006, provisional application No. 60/894,537, filed on Mar. 13, 2007, provisional application No. 60/956,947, filed on Aug. 21, 2007, provisional application No. 60/956,950, filed on Aug. 21, 2007.

(51) Int. Cl.
*A61M 15/00* (2006.01)

(52) U.S. Cl.
USPC ................. 128/200.23; 128/200.12

(58) Field of Classification Search
USPC ............ 128/200.11–200.14, 200.23
See application file for complete search history.

(56) References Cited

U.S. PATENT DOCUMENTS 6,390,088 B1 * 5/2002 Nohl et al. ............... 128/200.23
2003/0089368 A1   5/2003 Zhao
(Continued)

FOREIGN PATENT DOCUMENTS

EP   1787668 B1   5/2007
GB   1219090      1/1971
(Continued)

OTHER PUBLICATIONS

Instructions dated Aug. 21, 2012 for Japanese Application No. 2009-525059 in response to JPO Office Action dated Mar. 19, 2012.
(Continued)

Primary Examiner — Lynne Anderson
(74) Attorney, Agent, or Firm — Robert J. Smith

(57) ABSTRACT

An actuator for an inhaler for delivering medicament by inhalation, comprising: a housing for receiving a canister which comprises a body which includes a base and a head and defines a chamber containing medicament, and a valve stem which extends from the body and from which medicament is in use delivered on actuation of the canister; an outlet through which a user in use inhales; and a nozzle assembly which provides for delivery of medicament through the outlet, wherein the nozzle assembly comprises a nozzle block which receives the valve stem of the canister and, as a separately-formed component, a nozzle outlet which is fluidly connected to the nozzle block and includes an outlet orifice from which medicament is in use delivered.

33 Claims, 11 Drawing Sheets

(56) References Cited

U.S. PATENT DOCUMENTS

| | | | |
|---|---|---|---|
| 2004/0011357 A1* | 1/2004 | Braithwaite | 128/200.23 |
| 2005/0028814 A1* | 2/2005 | Robertson et al. | 128/200.23 |
| 2006/0076010 A1* | 4/2006 | King | 128/200.23 |
| 2006/0254581 A1* | 11/2006 | Genova et al. | 128/200.23 |

FOREIGN PATENT DOCUMENTS

| | | |
|---|---|---|
| GB | 1219090 A | 1/1971 |
| WO | 98/41254 A | 9/1998 |
| WO | 00/50112 A | 8/2000 |
| WO | 01/36033 A | 5/2001 |
| WO | 02/45783 A | 6/2002 |
| WO | WO 2006051073 A1 * | 5/2006 |

OTHER PUBLICATIONS

Main and Auxiliary Claim 1 filed concurrently with Instructions dated Aug. 21, 2012 for Japanese Application No. 2009-525059 in response to JPO Office Action dated Mar. 19, 2012.

English translation of JPO Office Action regarding Japanese Application No. 2009-525059 Mar. 19, 2012.

* cited by examiner

ACTUATOR FOR AN INHALER

CROSS-REFERENCE TO RELATED APPLICATIONS

The present application is filed pursuant to 35 USC 371 as a United States National Phase Application of International Patent Application Serial No. PCT/EP2007/058678 filed on 21 Aug. 2007, which claims priority from U.S. Provisional Application No. 60/823,134, filed 22 Aug. 2006, incorporated herein by reference in its entirety.

The disclosures of the following U.S. Provisional Applications are also incorporated herein by reference in their entirety: U.S. Provisional Application Nos. 60/823,139, 60/823,141, 60/823,143, 60/823,146, 60/823,151 and 60/823,154, all filed on 22 Aug. 2006; U.S. Provisional Application No. 60/894,537 filed on 13 Mar. 2007; and U.S. Provisional Application No. 60/956,947 entitled DRUG DISPENSER and U.S. Provisional Application No. 60/956,950 entitled DRUG DISPENSER both filed on 21 Aug. 2007.

The disclosures of the International (PCT) Patent Applications, simultaneously filed herewith under, which designate the United States of America and claim priority from the aforementioned U.S. Provisional Application Nos. 60/823,139, 60/823,141, 60/823,143, 60/823,146, 60/823,151 and 60/823,154, are all also incorporated by reference in their entirety:

FIELD OF THE INVENTION

The present invention relates to an actuator for use with an inhaler for administering drug by inhalation and to an inhaler including the same.

BACKGROUND OF THE INVENTION

It is known to provide an actuator for an inhaler (e.g. a metered dose inhaler (MDI)) for delivering drug by inhalation, which actuator comprises a housing arranged for receipt of a valved canister containing drug. The canister typically comprises a body, which includes a base and a head and defines a chamber, and a valve stem which extends from the body and from which drug is in use delivered on actuation of the canister. The actuator also comprises an outlet, which is arranged for receipt by the mouth or nose of a user and through which a user in use inhales. The actuator further comprises a nozzle assembly, which provides for delivery of drug through the outlet, wherein the nozzle assembly typically comprises a nozzle block which receives the valve stem of the canister.

In conventional actuators for use with MDI inhalers the nozzle block is provided as a single moulded part, which is usually moulded to be integral with the body of the actuator. The conventional nozzle block has an exit orifice from which aerosolized drug is expelled and thence, travels to an outlet (e.g. mouthpiece) for inhalation by a patient. Applicant finds that a more controlled passage of aerosolized drug (e.g. better channeling of drug plume) may be provided for where a nozzle outlet is provided as a separately-formed component to the nozzle block. The nozzle outlet is fluidly connected to the nozzle block and includes an outlet orifice from which drug is in use delivered. In addition, the nozzle outlet can be adapted to give a cleaner look to the outlet (i.e. mouthpiece) end of the actuator housing, which is also more amenable to cleaning by the patient.

Applicant finds that by use of such a 'two-part assembly' of nozzle block and nozzle outlet greater flexibility may be provided for in the overall design of the nozzle assembly. Thus, for example a more rigid (e.g. stubbier) nozzle block may be accommodated. Or alternatively, smaller jet orifice diameters (e.g. from 0.2 to 0.5 mm) may be accommodated. Additionally, different materials or combinations thereof may be use for the different parts of the nozzle assembly. The different materials may for example, be selected to have different finishes or electrostatic characteristics. Overall, the nozzle assembly is therefore much more readily tuned to provide the desired spray/travel characteristics of the aerosolized drug than is the conventional nozzle block. More ergonomic actuator forms may also be facilitated.

In addition, Applicant finds that by forming the nozzle assembly as a 'two-part assembly' the time of manufacture thereof may be simplified and speeded up. In more detail, the conventional single-part moulded stubby nozzle block of the well-known conventional MDI actuator requires a complex moulding tool and mould intervals of long pendency time. By contrast, the separate parts of the 'two part' assembly may be made simpler in form and thereby, made amenable to moulding thereof with shorter pendency times.

It is an aim of the present invention to provide an improved actuator for an inhaler for administering drug by inhalation and an inhaler including the same.

SUMMARY OF THE INVENTION

According to one aspect of the present invention there is provided an actuator for an inhaler for delivering drug by inhalation, comprising: a housing for receiving a canister which comprises a body which includes a base and a head and defines a chamber for containing drug, and a valve stem which extends from the body and from which drug is in use delivered on actuation of the canister; an outlet through which a user in use inhales; and a nozzle assembly which provides for delivery of drug through the outlet, wherein the nozzle assembly comprises a nozzle block for receiving the valve stem of the canister and, as a separately-formed component, a nozzle outlet which is fluidly connected to the nozzle block and includes an outlet orifice from which drug is in use delivered.

There is provided an actuator for an inhaler for delivering drug by inhalation by the oral or nasal route.

The actuator herein comprises a housing, which may have any suitable form but is suitably sized and shaped for ready accommodation by the hand of a patient. In particular, the housing is sized and shaped to enable one-handed operation of the inhaler.

The housing of the actuator herein is arranged for receipt of a canister. The canister comprises a body, which includes a base and a head and defines a chamber containing drug, and a valve stem which extends from the body and from which drug is in use delivered on actuation of the canister. In embodiments, the canister is formed from aluminium. The canister may be of the type well-known for use in metered dose inhaler (MDI) type inhaler devices.

The actuator comprises an outlet through which a user in use inhales. In embodiments, the outlet extends from the housing. The outlet is arranged for insertion into a body cavity of a patient. Where the patient body cavity is the mouth of a patient, the outlet is generally shaped to define a mouthpiece. Where the patient body cavity is the hose of a patient, the outlet is generally shaped in nozzle form for receipt by a nostril of the patient. In embodiments, the outlet may be provided with a removable protective cover such as a mouthpiece cover or nozzle cover.

The actuator comprises a nozzle assembly, which provides for delivery of drug through the outlet. The nozzle assembly comprises a nozzle block, which receives the valve stem of the canister.

The nozzle assembly also comprises, as a separately-formed component, a nozzle outlet which is fluidly connected to the nozzle block and includes an outlet orifice from which drug is in use delivered. In embodiments, the nozzle outlet is shaped to guide released (e.g. aerosolized) drug from the nozzle block to the outlet of the housing for inhalation by the patient. In embodiments, the end of nozzle outlet (i.e. that end that is not connected to the nozzle block) is shaped such as to mate up with the outlet of the housing.

In embodiments, the nozzle block is coupled to the housing. In embodiments, the nozzle block is integrally formed with the housing.

In embodiments, the outlet is formed separately of the housing. In embodiments, the nozzle outlet is coupled to the outlet. In embodiments, the nozzle outlet is integrally formed with the outlet.

In other embodiments, the outlet is integrally formed with the housing.

In embodiments, the nozzle block is coupled to the outlet. In embodiments, the nozzle block is integrally formed with the outlet.

In embodiments, the nozzle block includes a laterally-directed cavity which receives the nozzle outlet. In embodiments, the nozzle outlet is captively disposed in the laterally-directed cavity. The nozzle outlet is suitably held captive in the laterally-directed cavity by any suitable joining or sealing method such as by use of a press-fit or snap-fit method; by use of a clip engaging mechanism; by use of over-moulding; or by use of heat-staking. In embodiments, the nozzle outlet is a snap-fit in the laterally-directed cavity.

In embodiments, the laterally-directed cavity includes a recess and the nozzle outlet includes a projection which is captively engaged in the recess. In embodiments, the nozzle outlet is an interference fit in the laterally-directed cavity.

In embodiments, the outlet includes at least one air flow path which provides for a substantially annular air flow at an inner peripheral surface of the outlet on inhalation by the user through the outlet, such as to provide a sheathing air flow to an aerosol spray when delivered from the nozzle outlet. In embodiments, the annular air flow is in a direction away from the nozzle outlet. In embodiments, the outlet includes a plurality of air flow paths which together provide for the substantially annular air flow at the inner peripheral surface of the outlet.

In embodiments, the outlet has a closed rear section which partitions the outlet from the housing, such that, on inhalation through the outlet, an air flow is drawn only from an outer peripheral surface of the outlet. In one embodiment, the rear section of the outlet has an arcuate shape. In another embodiment, the rear section of the outlet has an elliptical shape.

In embodiments, the outlet comprises an external section which is configured to be gripped in the lips of the user and defines an open end through which drug is in use delivered and an internal section which defines the rear section to which the nozzle outlet is coupled.

In embodiments, the nozzle outlet includes a delivery channel which is fluidly connected to the outlet orifice and narrows towards the same. In one embodiment, the delivery channel has arcuate wall sections. In another embodiment, the delivery channel has substantially straight wall sections.

In embodiments, the at least one air flow path which provides for a substantially annular air flow at an inner peripheral surface of the outlet (on inhalation by the user through the outlet, such as to provide a sheathing air flow to an aerosol spray when delivered from the nozzle assembly) is enabled by the provision of one or more air inlets to the nozzle outlet, which nozzle outlet is in preferred embodiments integrally formed with the outlet. In embodiments, from 3 to 20, preferably from 3 to 10 air inlets are provided to the nozzle outlet. In embodiments, the combined (i.e. total when added together) cross-sectional area of the one or more air inlets is from 10 to 100 $mm^2$, such as from 15 to 85 $mm^2$, preferably from 20 to 45 $mm^2$. The velocity of the sheathing air flow, can be optimised (i.e. not too fast, not too slow) by optimising the value of the combined cross-sectional area. The one or more air inlets may adopt any suitable form including circular form cross-section, oval form cross-section, wedge form cross-section or slot form cross-section.

In embodiments, the nozzle outlet is essentially well or bucket-shaped (e.g. with a generally flat well or bucket base) and the outlet orifice and one or more air inlets thereof are provided to the base of the bucket. In embodiments, the one or more air inlets are arranged about the outlet orifice such that drug (e.g. spray form) released therethrough into the mouthpiece experiences the sheathing air flow. In embodiments, the one or more air inlets adopt a symmetric arrangement about the outlet orifice. In embodiments, the one or more air inlets adopt a radial (e.g. circular) arrangement about the outlet orifice. One preferred arrangement is a circular arrangement of from 3 to 10 circular air inlets arranged about the outlet orifice, which lies at the centre of the circular arrangement. Another preferred arranged is an arrangement of slot or wedge form air inlets radiating out from the outlet orifice, which lies at the centre of the radiating out arrangement.

In embodiments, the outlet orifice is a spray orifice which provides for delivery of an aerosol spray of drug.

In embodiments, at least a rear section of the outlet has an increasing internal dimension in a direction away from the nozzle assembly. In one embodiment, the outlet defines an essentially cone-shaped interior. In another embodiment, the outlet defines an essentially bucket-shaped interior.

In embodiments, the outlet is a mouthpiece. In embodiments, the outlet (e.g. mouthpiece) is arranged to be replaceable. In embodiments, the outlet (e.g. mouthpiece) is formed by a dual-moulding process with materials of construction selected for user comfort and/or grip thereof.

In embodiments, the outlet (e.g. mouthpiece) takes the form of a spacer. That is to say, it is formed to have an elongated and/or widened form, which provides a spacing volume within which the released aerosolised drug may expand.

The nozzle assembly and/or the nozzle block and/or the nozzle outlet may be formed of different materials and to different specifications which are specifically suited to their purposes. Examples of suitable materials include plastic polymeric materials such as polypropylene, ABS, HDPE and polycarbonate and metal materials including stainless steel. Optionally, the plastic polymeric materials may be filled with anti-static agents such as by means of a moulding or coating (e.g. post-finishing) process. Embodiments are envisaged in which different parts are composed of different materials such as to optimise the overall performance of the nozzle.

The present invention also extends to an inhaler comprising the above-described actuator and a canister for containing drug.

The present invention further extends to a kit of parts comprising the above-described actuator and a canister for containing drug receivable thereby.

The inhaler of the invention is suitably of the well-known "metered dose inhaler" (MDI) type, and more suitably a hand-held, hand-operable breath-coordinated MDI. In such a MDI, the patient manually actuates the MDI for release of the drug from the canister while concurrently inhaling at the outlet. Thus inhalation and actuation are coordinated. This is in distinction from breath-operated MDIs, where the inhalation event itself actuates the MDI so that no coordination is required.

Additional aspects and features of the present invention are set forth in the claims and in the description of exemplary embodiments of the present invention which now follow with reference to the accompanying Figures of drawings. Such exemplary embodiments may or may not be practiced mutually exclusive of each other, whereby each embodiment may incorporate one or more features of one or more of the other embodiments. It should be appreciated that the exemplary embodiments are set forth to illustrate the invention, and that the invention is not limited to these embodiments.

DETAILED DESCRIPTION OF THE DRAWINGS

Figure 1:
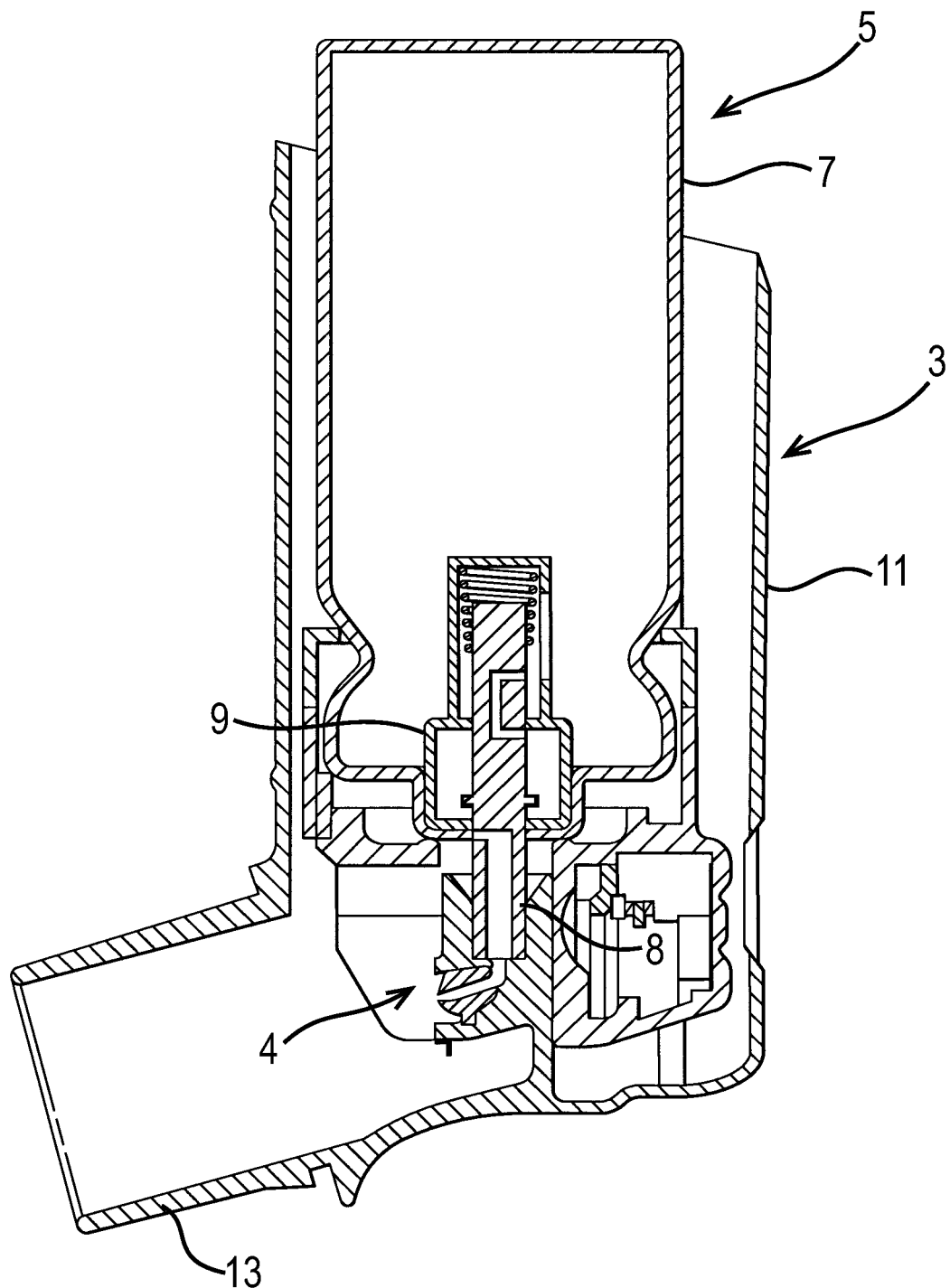
FIG. 1 illustrates a vertical sectional view of a hand-held, hand-operable breath-coordinated, metered dose inhaler (MDI) in accordance with a first embodiment of the present invention.
Figure 2:
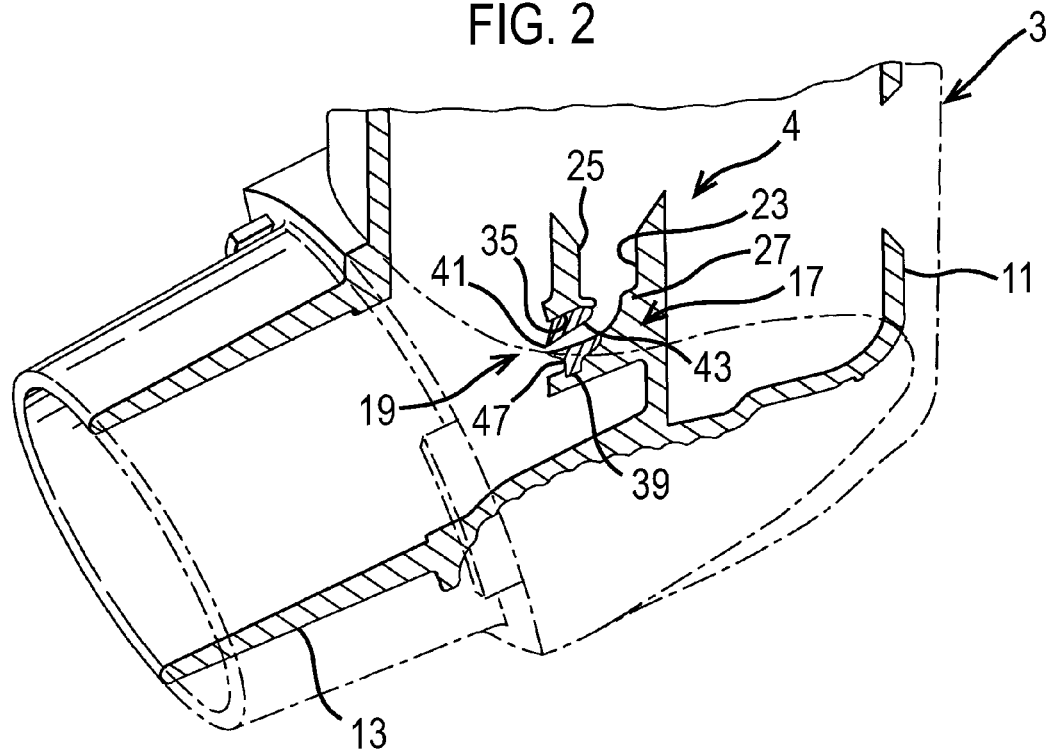
FIG. 2 illustrates in enlarged scale a fragmentary vertical sectional view of the lower end of the actuator of the inhaler of FIG. 1.
Figure 3:
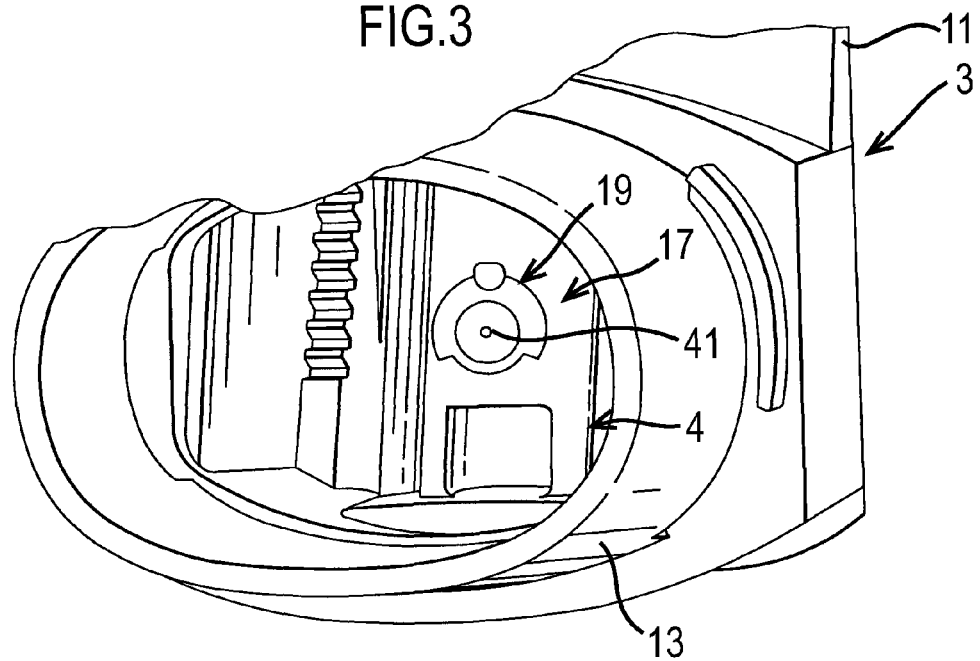
FIG. 3 illustrates in enlarged scale a fragmentary perspective view of the actuator of the inhaler of FIG. 1.

FIGS. 1 to 3 illustrate an inhaler in accordance with a first embodiment of the present invention.

The inhaler comprises an actuator which comprises a main body 3 and a nozzle assembly 4 which is coupled to the main body 3 and provides for the delivery of an aerosol spray of a drug on actuation of the inhaler, and an aerosol canister 5 which contains drug to be delivered on actuation of the inhaler and is fitted in the main body 3 and fluidly connected to the nozzle assembly 4.

The canister 5 comprises a body 7 which defines a chamber which contains a drug in a propellant under pressure, a valve stem 8 which extends from one end, the head, of the body 7 and an internal metering valve 9 which is normally biased to a closed position and opened to deliver a metered dose of drug from the canister 5 when the valve stem 8 is depressed into the body 7.

In this particular embodiment, the canister 5 is made of metal, for instance of stainless steel or, more preferably, of aluminium or an aluminium alloy. The canister contains a pressurised medicinal aerosol formulation. The formulation comprises the drug (one or more drug actives) and a fluid propellant, and optionally one or more excipients and/or adjuvants. The drug is in solution or suspension in the formulation. The propellant is typically a CFC-free propellant, suitably a liquid propellant, and preferably is a HFA propellant, such as HFA-134a or HFA-227 or a combination thereof. The drug active(s) is of the type for use in treatment of a respiratory disease or condition, such as asthma or chronic obstructive pulmonary disease (COPD). The active(s) may also be for prophylaxis or palliation of a respiratory disease or condition.

The canister 5 may have its inner surface coated with a fluorocarbon polymer, optionally in a blend with a non-fluorocarbon polymer, such as a blend of polytetrafluoroethylene and polyethersulphone (PTFE-PES), as disclosed in U.S. Pat. Nos. 6,143,277; 6,511,653; 6,253,762; 6,532,955; and 6,546, 928. This is particularly preferred if the drug is in suspension in the formulation, and especially if the suspension formulation is composed only, or substantially only, of the drug and HFA propellant.

The valve stem 8 forms part of a metering valve, as will be understood by the skilled person in the art, and as commercially available from manufacturers well known in the aerosol industry, for example, from Valois, France (e.g. DF10, DF30, DF60), Bespak plc, UK (e.g. BK300, BK356, BK357) and 3M-Neotechnic Ltd, UK (e.g. Spraymiser™). Embodiments of metering valves are set forth in U.S. Pat. Nos. 6,170,717; 6,315,173; and 6,318,603. The metering chamber of the metering valve may be coated with a fluorinated polymer coating, such as formed from perfluoro-hexane, for instance by cold plasma polymerisation, as detailed in US-A-2003/0101993.

The canister 5 may also be associated with an actuation indicator or dose indicator for example, as disclosed in US-A-2006/0096594.

This description of the canister 5 applies equally to the canister in the other exemplary embodiments of the invention described below.

The main body 3 comprises a housing 11 in which the canister 5 is in use fitted, and a mouthpiece 13, in this embodiment a tubular element, which is in fluid communication with a lower end of the housing 11 and in use is gripped in the lips of the user. In one embodiment the housing 11 and the mouthpiece 13 are integrally formed, preferably of a plastics material.

The nozzle assembly 4 comprises a nozzle block 17, in this embodiment disposed to a base surface of the housing 11, for receiving the valve stem 8 of the canister 5, and a nozzle outlet 19 which is a component formed separately of the nozzle block 17 and fluidly connected to the nozzle block 17, such as to provide for the delivery of an aerosol spray of drug through the mouthpiece 13. In one embodiment the nozzle block 17 is integrally formed with the housing 11 and the mouthpiece 13 of the main body 3.

The nozzle block 17 includes a tubular bore 23 for receiving the valve stem 8 of the canister 5, which in this embodiment is co-axial with the longitudinal axis of the housing 11.

The tubular bore 23 is open at one, the upper, end thereof and includes an upper section 25 which has an internal dimension which is substantially the same as the outer dimension of the valve stem 8 of the canister 5 and a lower section 27 which has a smaller dimension, which sections 25, 27 together define an annular seat for the distal end of the valve stem 8.

The nozzle block 17 includes a laterally-directed cavity 35 which receives the nozzle outlet 19 and is fluidly connected to the tubular bore 23 thereof.

In this embodiment the nozzle outlet 19 is configured to be a snap-fit in the laterally-directed cavity 35 in the nozzle block 17.

In this embodiment the laterally-directed cavity 35 in the nozzle block 17 includes a recess 39 in the peripheral surface thereof which receives a projection 47 on the nozzle outlet 19, such as to provide for the nozzle outlet 19 to be held captively in sealing engagement with the laterally-directed cavity 35.

The nozzle outlet 19 includes a spray orifice 41 which provides for the delivery of an aerosol spray of drug and a delivery channel 43 which is fluidly connected to the spray orifice 41.

In this embodiment the delivery channel 43 is a tapering channel which narrows towards the spray orifice 41. In this embodiment the delivery channel 43 has arcuate wall sections. Further, in this embodiment the nozzle block 17 has no expansion chamber directly underneath the tubular bore 23 thereof (c.f. the embodiment of FIG. 5, which has a defined expansion chamber 149 portion directly underneath the tubular bore 133 thereof).

With this configuration of the nozzle assembly 4, the nozzle block 17 and the nozzle outlet 19 can be formed of different materials and to different specifications which are specifically suited to their purposes.

In one embodiment the nozzle block 17 can be formed of a relatively rigid material, such as a hard plastics material, which resists deflection, as would normally occur on actuation of the inhaler by depression of the body 7 of the canister 5 relative to the main body 3 of the actuator. The generally stubby shape of the nozzle block 17 may also be noted, which also assists in resisting deflection thereof during actuation. Applicant realizes that such resistance to deflection can give rise to more consistent delivery of drug, which can also provide better fine particle mass (FPM) delivery characteristics.

In one embodiment the nozzle outlet 19 can be fabricated to a higher tolerance and to a different design than could be achieved where integrally formed with the nozzle block 17, as done in the prior art devices.

In one embodiment the inhaler further comprises a mouthpiece cap (not illustrated) which provides for closure of the mouthpiece 13.

Figure 4:
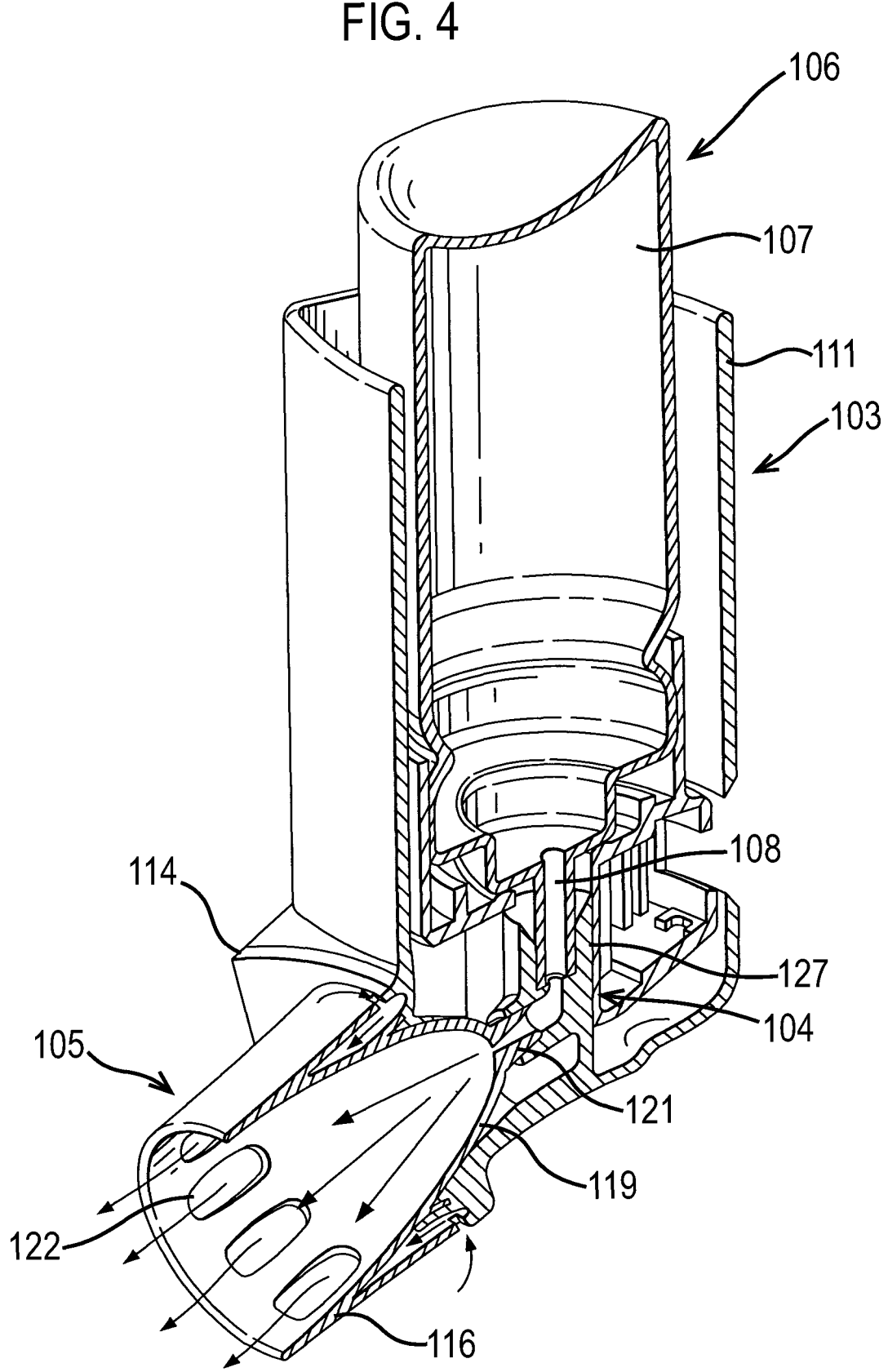
FIG. 4 illustrates a vertical sectional view of a hand-held, hand-operable breath-coordinated MDI in accordance with a second embodiment of the present invention.
Figure 5:
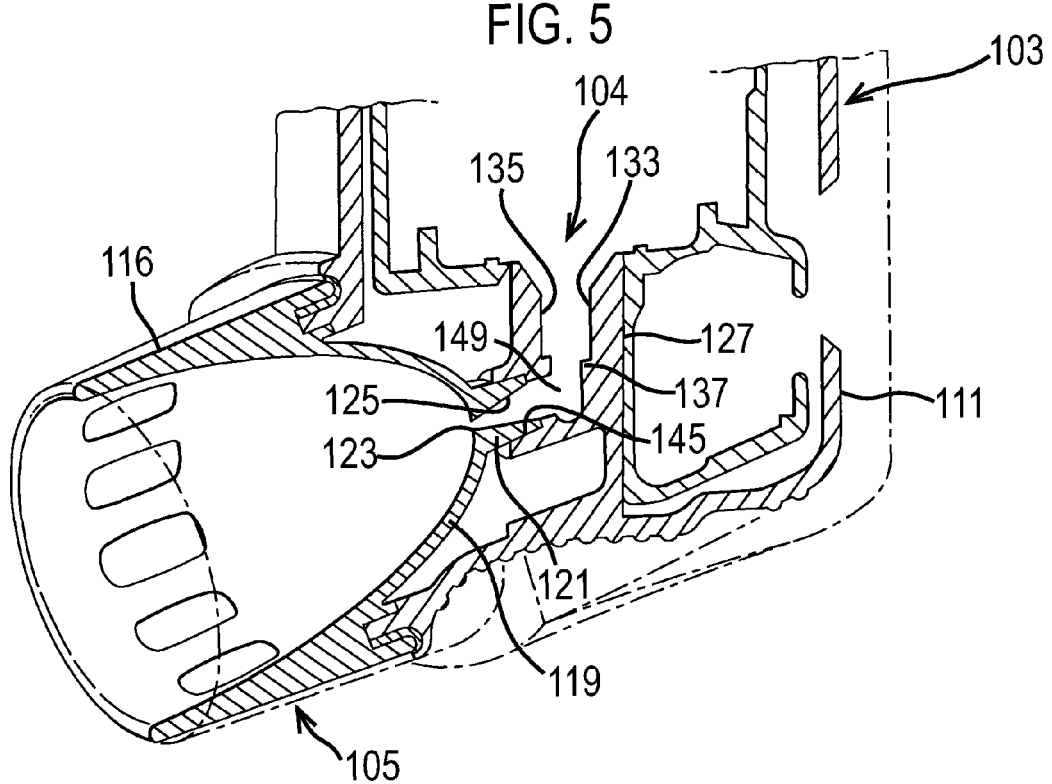
FIG. 5 illustrates in enlarged scale a fragmentary vertical sectional view of the lower end of the actuator of the inhaler of FIG. 4.
Figure 6:
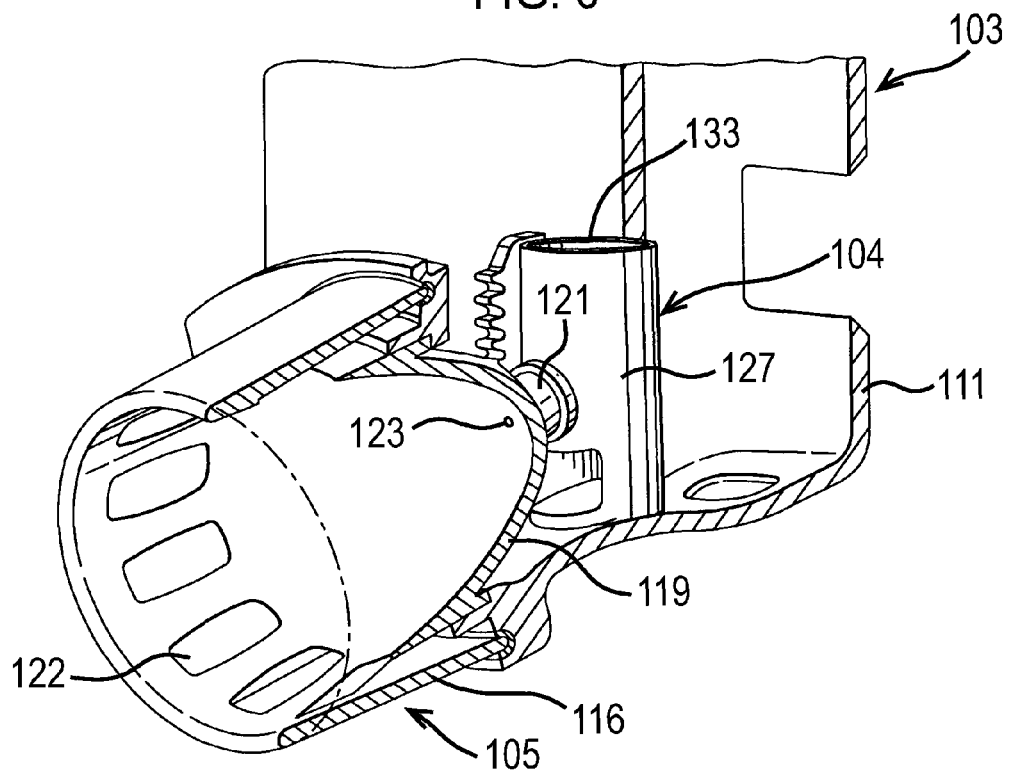
FIG. 6 illustrates in enlarged scale a fragmentary perspective view of the actuator of the inhaler of FIG. 4.

FIGS. 4 to 6 illustrate an inhaler in accordance with a second embodiment of the present invention.

The inhaler comprises an actuator which comprises a main body 103, a nozzle assembly 104 which is coupled to the main body 103 and provides for the delivery of an aerosol spray of a drug on actuation of the inhaler, and a mouthpiece 105 which is coupled to a lower end of the main body 103 and in use is gripped in the lips of the user, and an aerosol canister 106 which contains drug to be delivered on actuation of the inhaler and is fitted in the main body 103 and fluidly connected to the nozzle assembly 104.

The canister 106 comprises a body 107 which defines a chamber which contains a drug in a propellant under pressure, a valve stem 108 which extends from one end, the head, of the body 107 and an internal metering valve (not illustrated) which is normally biased to a closed position and opened to deliver a metered dose of drug from the canister 106 when the valve stem 108 is depressed into the body 107.

The main body 103 comprises a housing 111 in which the canister 106 is in use fitted, and a sealing member 114 which provides for sealing engagement of the mouthpiece 105 and the housing 111, such that the mouthpiece 105 is internally partitioned from the housing 111 and an air flow as drawn through the mouthpiece 105 on inhalation by a user is drawn from an outer peripheral surface of the mouthpiece 105. In this embodiment the housing 111 and the sealing member 114 are formed as separate components, but could in another embodiment be integrally-formed.

The mouthpiece 105 comprises an external section 116 which is configured to be gripped in the lips of a subject and defines a substantially cylindrical, open forward end through which an aerosol spray of a drug is in use delivered on actuation of the inhaler, an internal section 119 which has a closed rear section, and a nozzle outlet 121 which is coupled to a rear end of the internal section 119, such as to provide for the delivery of an aerosol spray into and through the internal section 119.

In this embodiment the external and internal sections 116, 119 are configured such as to define at least one, in this embodiment a plurality of air flow paths 122 which provide for a substantially annular air flow at the inner peripheral surface of the mouthpiece 105 which sheaths the aerosol spray as delivered from the nozzle outlet 121, thereby entraining the aerosol spray and reducing deposition at the internal surface of the mouthpiece 105.

In this embodiment the rear section of the internal section 119 has an arcuate shape, here an elliptical shape.

The nozzle outlet 121 includes a spray orifice 123 which provides for the delivery of an aerosol spray through the internal section 119 of the mouthpiece 105 and a delivery channel 125 which is fluidly connected to the spray orifice 123.

In this embodiment the delivery channel 125 is a tapering channel which narrows towards the spray orifice 123. In this embodiment the delivery channel 125 has straight wall sections.

In this embodiment the mouthpiece 105 comprises a single, integral component, typically as formed from a plastic polymer material.

The nozzle assembly 104 comprises a nozzle block 127, in this embodiment disposed to a base surface of the housing 111, for receiving the valve stem 108 of the canister 106, and the nozzle outlet 121 of the mouthpiece 105 which is fluidly connected to the nozzle block 127, such as to provide for the delivery of an aerosol spray through the mouthpiece 105. In one embodiment the nozzle block 127 is integrally formed with the housing 111 of the main body 103.

The nozzle block 127 includes a tubular bore 133 for receiving the valve stem 108 of the canister 106, which in this embodiment is co-axial with the longitudinal axis of the housing 111. The tubular bore 133 is open at one, the upper, end thereof and includes an upper section 135 which has an internal dimension which is substantially the same as the outer dimension of the valve stem 108 of the canister 106 and a lower section 137 which has a smaller dimension, which sections 135, 137 together define an annular seat for the distal end of the valve stem 108. In this embodiment, the nozzle block is provided with a distinct expansion chamber 149 portion positioned directly underneath the tubular bore 133 thereof.

The nozzle block 127 includes a lateral cavity 145 which receives the nozzle outlet 121 of the mouthpiece 105 and is fluidly connected to the tubular bore 133 thereof.

In this embodiment the nozzle outlet 121 is configured to be a tight friction fit in the lateral cavity 145 in the nozzle block 127. Desirably, the tight friction fit provides a gas-tight seal. In other embodiments, other types of sealing method, also preferably arranged to provide a gas-tight seal, may be employed.

With this configuration of the nozzle assembly 104, the nozzle outlet 121 and the nozzle block 127 can be formed of different materials and to different specifications which are specifically suited to their purposes.

In one embodiment the nozzle outlet 121 can be fabricated to a higher tolerance and to a different design than could be achieved where integrally formed with the nozzle block 127, as done in the prior art devices.

In one embodiment the nozzle block 127 can be formed of a relatively rigid material, such as a hard plastics material, which resists deflection, as would normally occur on actuation of the inhaler by depression of the body 107 of the canister 106 relative to the main body 103 of the actuator.

In one embodiment the inhaler further comprises a mouthpiece cap (not illustrated) which provides for closure of the mouthpiece 105.

In one modification of the second-described embodiment the nozzle block 127 could be coupled with the mouthpiece 105, such as to be removable therewith.

In another modification of the second-described embodiment the mouthpiece 105 could be modified to omit the at least one peripheral air flow path 122 and instead have an open rear section, such that an air flow is drawn through the mouthpiece 105 from the housing 111 in the conventional manner.

Figure 7:
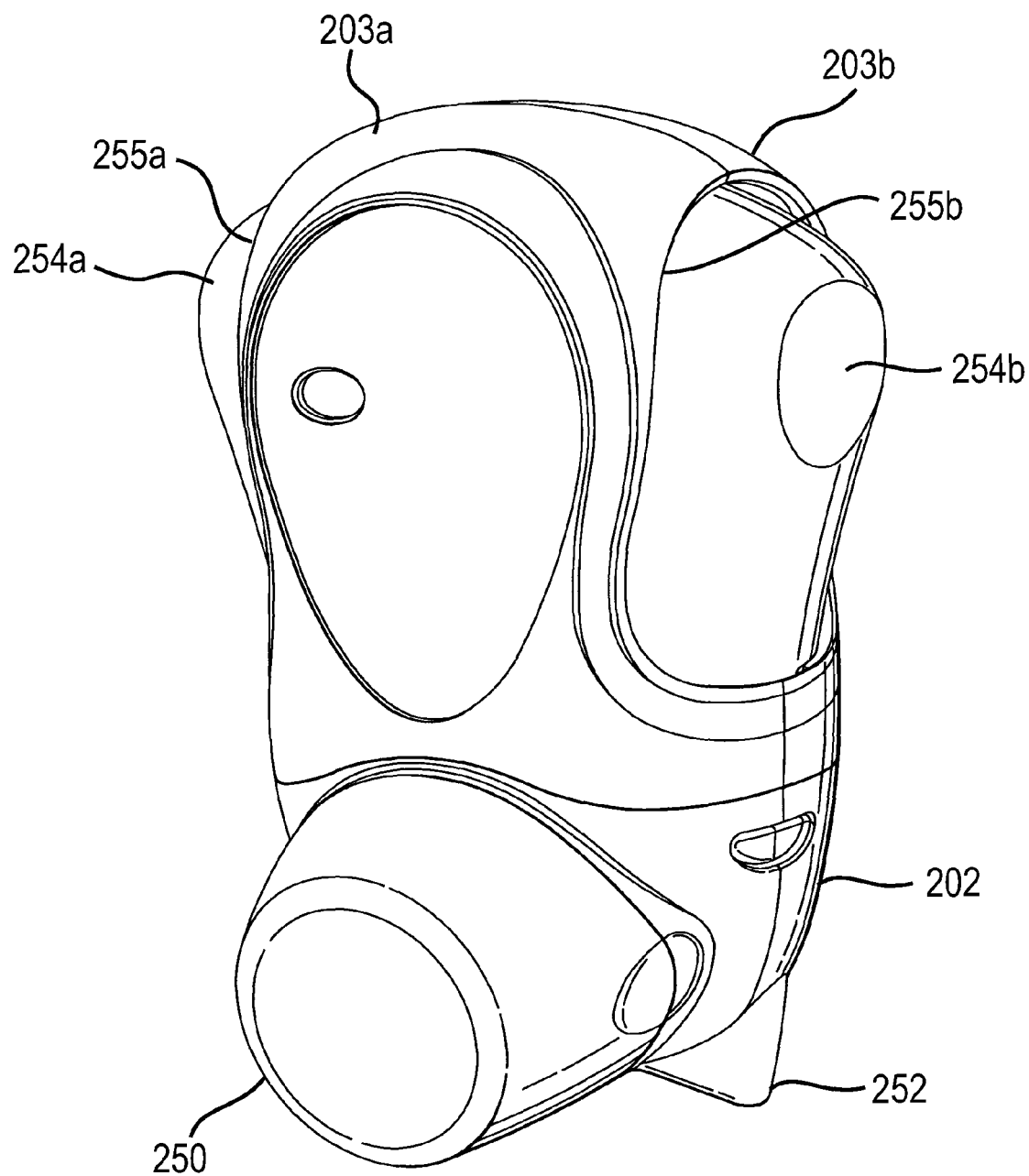
FIG. 7 illustrates a perspective view of a hand-held, hand-operable breath-coordinated MDI in accordance with a third embodiment of the present invention.
Figure 8:
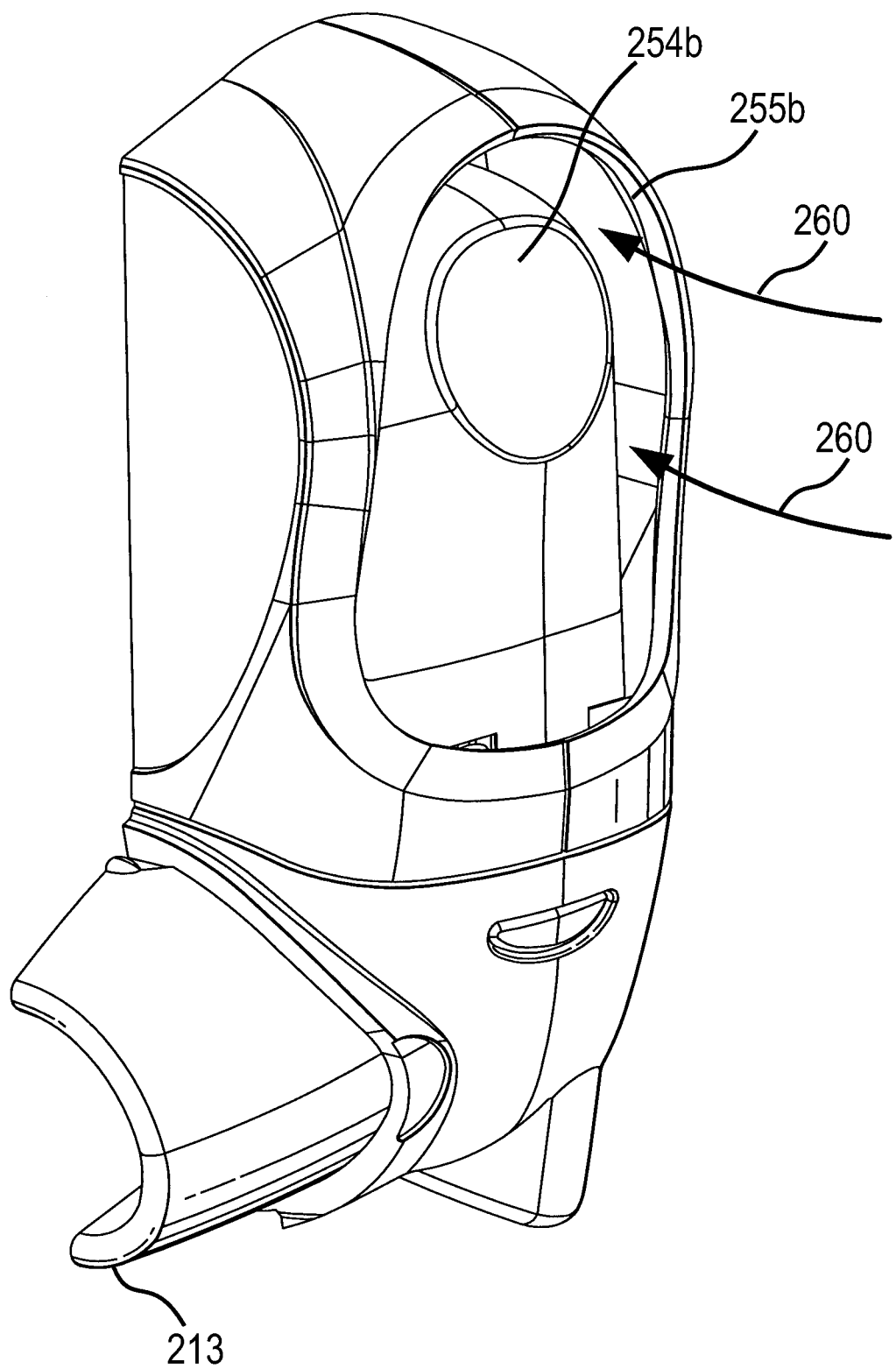
FIG. 8 illustrates a perspective view of a first half of the actuator of FIG. 7 showing air flow into the inhaler body in the 'in use' position thereof.
Figure 9:
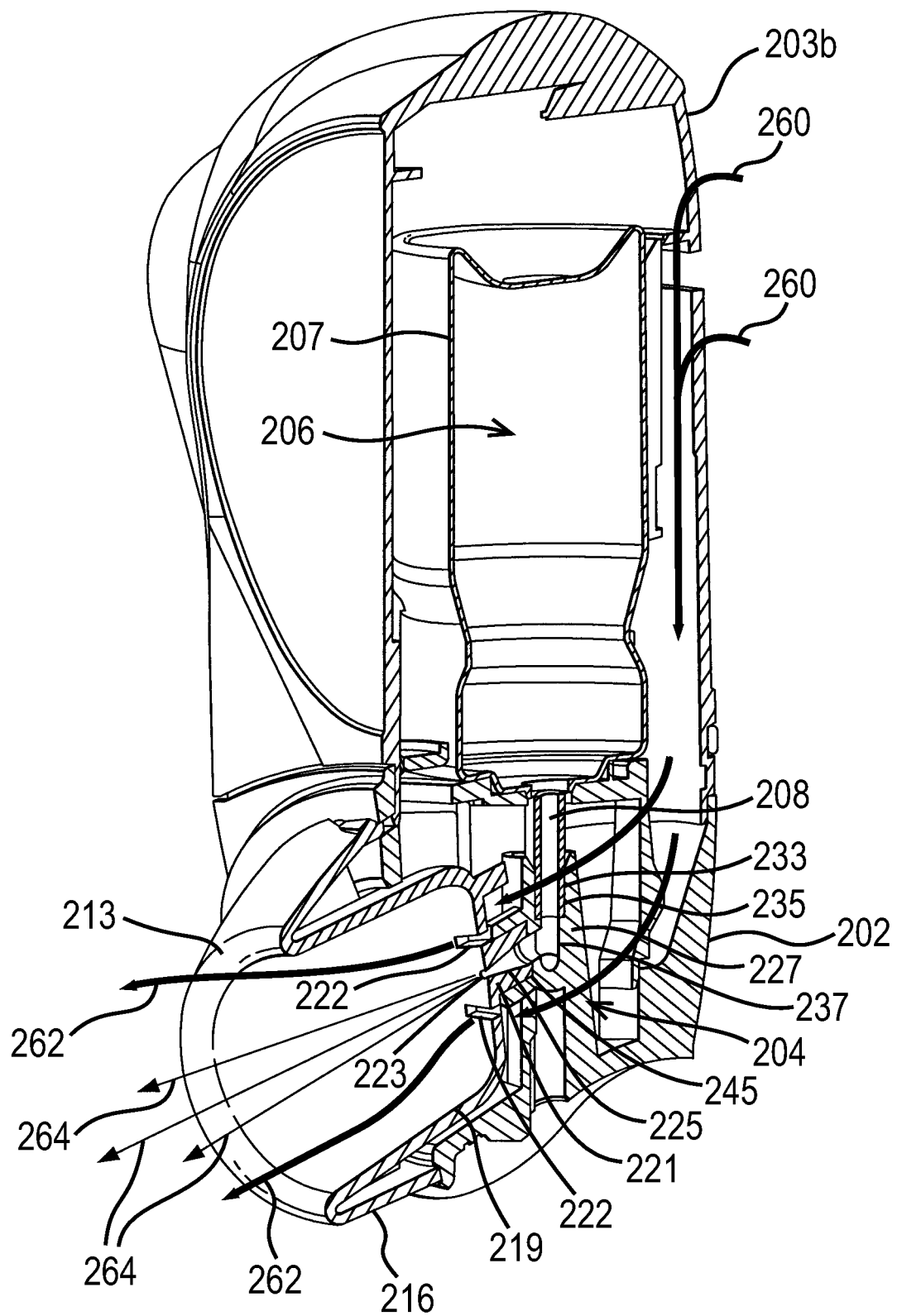
FIG. 9 illustrates a perspective cut-away view of a second half of the actuator of FIG. 7 showing air flow through the inhaler body in the 'in use' position thereof.

FIGS. 7 to 9 illustrate aspects of an inhaler in accordance with a third embodiment of the present invention.

FIG. 7 shows an inhaler herein comprising a housing that is defined in combination by front 203a and rear 203b upper housing parts and lower housing part 202, all of which are suitably formed from plastic. It will be noted that the overall form of the housing is arranged for ease of receipt by a user's hand such that in general terms the rear of lower housing part 202 is received by the user's palm. Mouthpiece 213 (not visible in FIG. 7, but see FIG. 8) is protected by removable mouthpiece cover 250, which extends from the front of lower housing part 202 and is arranged in use, for insertion into the mouth of a patient for inhalation there through. A ledge 252 is provided to the base of the lower housing part 202 such that the device may be arranged to 'stand upright' on the ledge 252 and mouthpiece cover 250. The mouthpiece cover 250 may take the form described in Applicant's co-pending PCT Patent Application No. WO-A-2007/028992, which claims priority from UK patent application no. 0518355, the entire contents of both of which are incorporated herein by reference.

As shown in FIG. 7 the upper housing parts 203a, 203b are permanently fixed to each other and to the lower housing part 202. In alternative embodiments, the upper housing parts 203a, 203b are permanently fixed to each other but reversibly fixed to the lower housing part 202 by a suitable reversible fixing mechanism such that the upper parts 203a, 203b may be reversibly removed from the lower part 202 to allow access of the interior thereof. Such alternative embodiments are particularly suitable where the inhaler is arranged to be rechargeable by replacing an exhausted drug canister (see canister 206 of FIG. 9) by a fresh one. Suitable reversible fixing mechanisms include screw fixing mechanisms; and push and/or snap-fit fixing mechanisms.

Opposing levers 254a, 254b protrude from apertures 255a, 255b provided to the front 203a and rear 203b upper housing parts. The levers 254a, 254b are shaped such as to respectively accommodate the finger and thumb of a patient in use, thereby facilitating one-handed operation of the device. In essence, the levers 254a, 254b are arranged such that the inhaler may be fired in response to a patient pushing the levers 254a, 254b towards each other, typically by a finger and thumb squeezing action. In embodiments, the levers 254a, 254b are formed by a dual-moulding process with materials of construction selected for user comfort and/or grip thereof.

FIG. 8 shows one half of the actuator of FIG. 7 in the 'in use' position, in which the mouthpiece 213 has been revealed, and in which lever 254b has been pushed inwards to open up aperture 255b. External air 260 may thus, now be drawn into the body of the inhaler housing through this aperture 255b (and also similarly through aperture 255a on the other side) in response to patient inhalation through the mouthpiece 213.

FIG. 9 illustrates in more detail, the inner workings of the inhaler of FIG. 7 and in particular, the air flow 260, 262 through the inhaler body, which is again shown in the 'in use' position thereof.

Referring to FIG. 9 in more detail, the inhaler may be seen to comprise a nozzle assembly 204 which is coupled to the lower body part 202 and provides for the delivery of an aerosol spray of a drug on actuation of the inhaler. Mouthpiece 213 is also coupled to a lower body part 202 and in use is gripped in the lips of the user to facilitate oral inhalation. Received within the inhaler there is aerosol canister 206 which contains drug to be delivered on actuation of the inhaler and is fitted in the main body and fluidly connected to the nozzle assembly 204.

The canister 206 comprises a body 207 which defines a chamber which contains a drug in a propellant under pressure, a valve stem 208 which extends from one end, the head, of the body 207 and an internal metering valve (not illustrated) which is normally biased to a closed position and opened to deliver a metered dose of drug from the canister 206 when the valve stem 208 is depressed into the body 207.

The mouthpiece 213 comprises an external section 216 which is configured to be gripped in the lips of a subject and defines a substantially cylindrical, open forward end through which an aerosol spray of a drug is in use delivered on actuation of the inhaler, an essentially 'bucket-shaped' internal section 219 which has a closed rear section (other than air holes 222 and spray orifice 223 described hereinafter), and a nozzle outlet 221 which is coupled to a rear end of the internal section 219, such as to provide for the delivery of an aerosol spray into and through the internal section 219. The mouthpiece 213 in this embodiment is a separately-formed component part of the inhaler which is assembled to connect to the nozzle block 227.

In use of this embodiment of the inhaler herein, air 260 is drawn down the rear part 203b of the body of the inhaler past around the nozzle assembly 204 and towards the rear of the internal section 219 of the mouthpiece, which is provided with dual horizontal slot-like air holes 222 at the rear (i.e. base of the 'bucket') thereof arranged about spray orifice 223. The air holes 222 may be equi-spaced from the spray orifice 223. As may be seen, when the air 260 is drawn through these dual air holes 222 a duality of air flows 262 is defined within the mouthpiece 213. This provides for a partly annular air flow at the inner peripheral surface of the mouthpiece 213, which partly sheaths the aerosol spray 264 as delivered from the spray orifice 223 of the nozzle outlet 221, thereby entraining the aerosol spray and reducing deposition at the internal surface of the mouthpiece 213.

In this embodiment the rear of the internal section 219 has a generally flat shape, which forms the base of the 'bucket'.

The edges of the base curve outwards such that the internal section 219 has an increasing internal dimension in a direction away from the nozzle assembly 204.

The nozzle outlet 221 includes the spray orifice 223 which provides for the delivery of an aerosol spray through the internal section 219 of the mouthpiece 213 and a delivery channel 225 which is fluidly connected to the spray orifice 223.

In this embodiment the delivery channel 225 is a tapering channel which narrows towards the spray orifice 223. In this embodiment the delivery channel 225 has straight wall sections.

In this embodiment, the nozzle assembly 204 comprises a nozzle block 227 for receiving the valve stem 208 of the canister 206, and the nozzle outlet 221 of the mouthpiece 213 which is fluidly connected to the nozzle block 227, such as to provide for the delivery of an aerosol spray through the mouthpiece 213. In this embodiment the nozzle block 227 is integrally formed with the lower body part 202.

The nozzle block 227 includes a tubular bore 233 for receiving the valve stem 208 of the canister 206, which in this embodiment is co-axial with the longitudinal axis of the housing. The tubular bore 233 is open at one, the upper, end thereof and includes an upper section 235 which has an internal dimension which is substantially the same as the outer dimension of the valve stem 208 of the canister 205 and a lower section 237 which has a smaller dimension, which sections 235, 237 together define an annular seat for the distal end of the valve stem 208.

In this embodiment, the nozzle block 227 includes a lateral cavity 245 which receives the nozzle outlet 221 of the mouthpiece 213 and is fluidly connected to the tubular bore 233 thereof. The nozzle outlet 221 is configured to be a tight friction fit in the lateral cavity 245 in the nozzle block 227. Desirably, the tight friction fit provides a gas-tight seal. In other embodiments, other types of sealing method, also preferably arranged to provide a gas-tight seal, may be employed.

With this configuration of the nozzle assembly 204, the nozzle outlet 221 and the nozzle block 227 can be formed of different materials and to different specifications which are specifically suited to their purposes.

The levers 254a, 254b may result in release of drug from the canister 206 through co-operation with a mechanism attached to the canister 206 as described in U.S. provisional application No. 60/823,139 filed 22 Aug. 2006 and the International (PCT) Patent Application claiming priority therefrom which designates the United States of America and is filed simultaneously herewith under; U.S. provisional application No. 60/894,537 filed 13 Mar. 2007; and the two US provisional applications entitled DRUG DISPENSER also filed simultaneously herewith respectively under; all of which applications are hereby incorporated herein in their entirety by reference.

Figure 10:
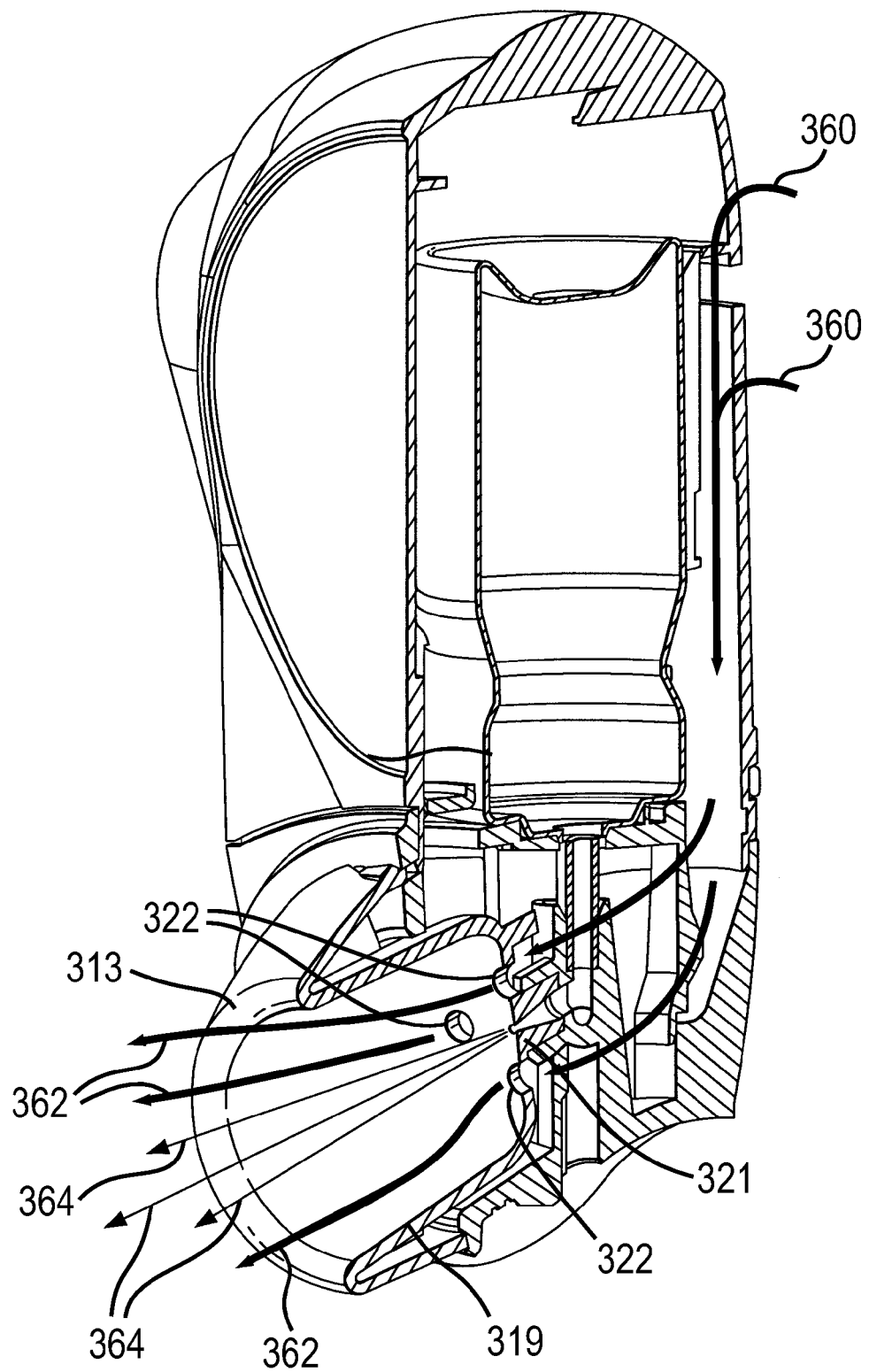
FIG. 10 illustrates a perspective cut-away view of a second half of an actuator that is a slight variation of that third embodiment of FIGS. 7-9 showing air flow through the inhaler body in the 'in use' position thereof.

FIG. 10 shows a variation of the third embodiment of the inhaler device of FIGS. 7-9, which is identical to that third embodiment in all aspects other that the dual horizontal slot-like air holes 222 of the third embodiment are replaced by an arrangement of four circular air holes 322 (only three visible in FIG. 10) about the spray orifice 322 at the rear (i.e. base of the 'bucket') of the internal section 319 of the mouthpiece 313. It may be seen that the four air holes 322 are arranged in a generally circular arrangement about the spray orifice, in this embodiment being at 90° angular displacement relative to each other. The spray orifice may be centrally located in the circular arrangement of the air holes 322. The combined (i.e. total when added-up) cross-sectional area of the four circular air holes 322 is from 20 to 45 mm$^2$. As may be seen in FIG. 10, when the air 360 is drawn through these plural spaced air holes 322 a plurality of air flows 362 is defined within the mouthpiece 313. This provides for an essentially annular air flow at the inner peripheral surface of the mouthpiece 313, which essentially sheaths the aerosol spray 364 as delivered from the spray orifice of the nozzle outlet 321, thereby entraining the aerosol spray and reducing depoisition at the internal surface of the mouthpiece 313.

In variations of the embodiment of FIG. 10, the symmetric, circular arrangement of four air holes 322 is replaced by a symmetric, circular arrangement of three or from five to ten air holes 322. In other variations of the embodiment of FIG. 10, the symmetric, circular arrangement of four air holes 322 is replaced by a symmetric, radiating-out arrangement of from three to ten wedge or slot form air holes 322.

Figure 11A:
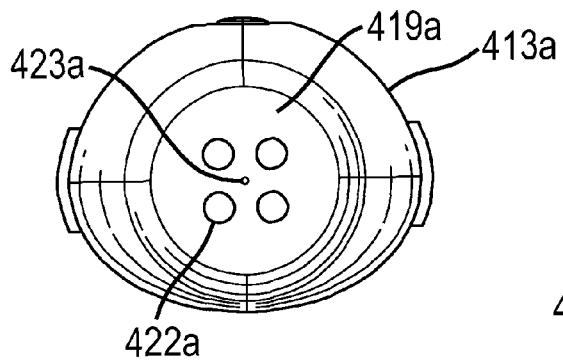
FIGS. 11a to 11n respectively show front views of mouthpiece forms, which may be employed in the drug dispenser devices of FIG. 7-9 or 10 as an alternative to the mouthpieces thereof.
Figure 11B:
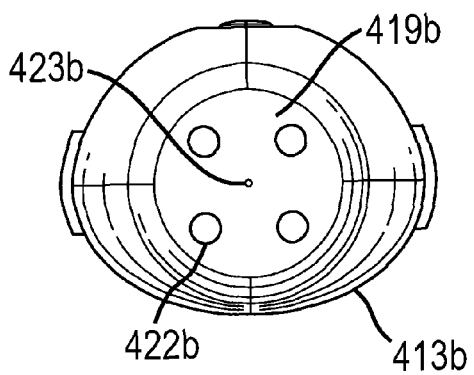
Figure 11C:
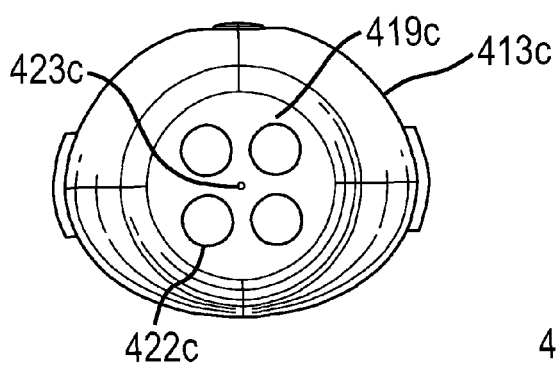
Figure 11D:
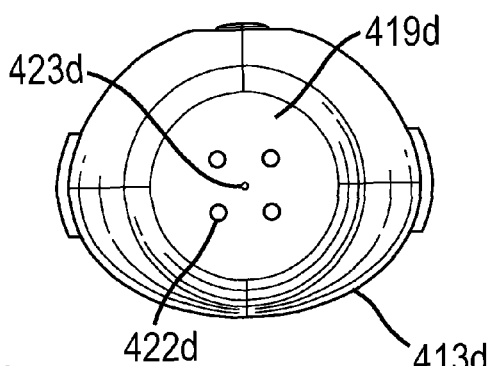
Figure 11E:
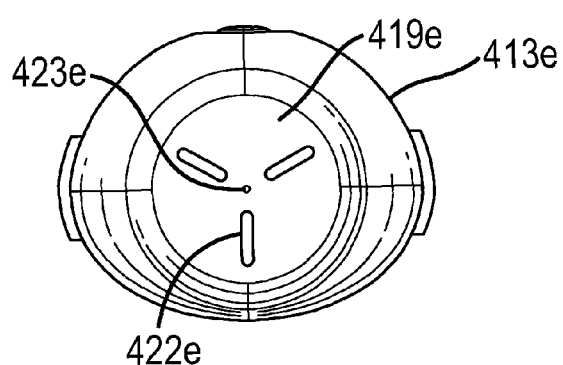
Figure 11F:
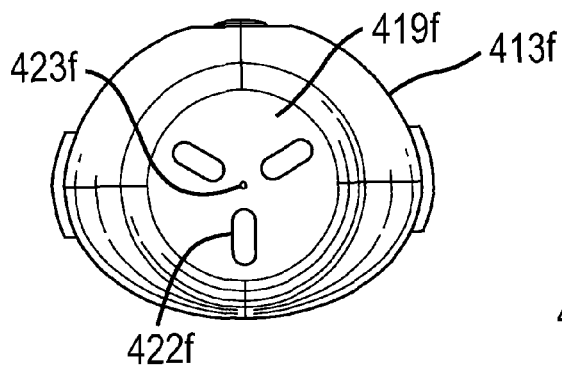
Figure 11G:
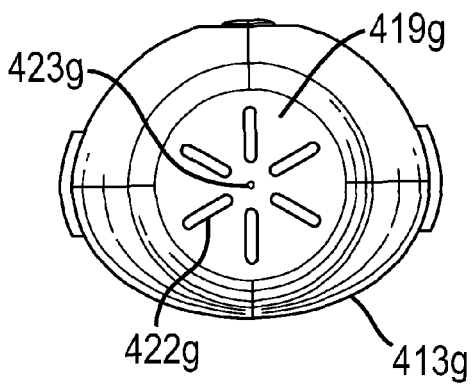
Figure 11H:
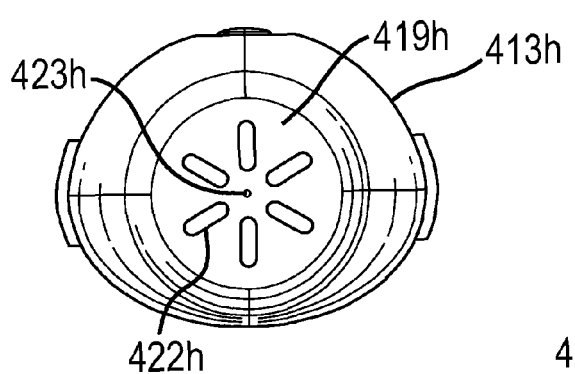
Figure 11I:
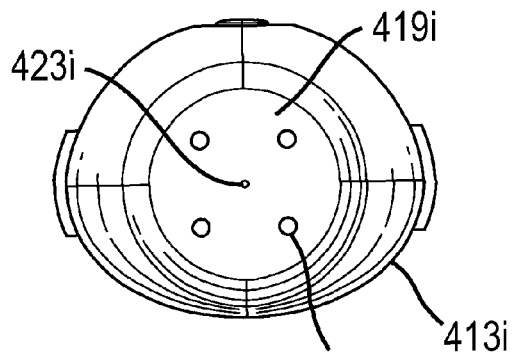
Figure 11J:
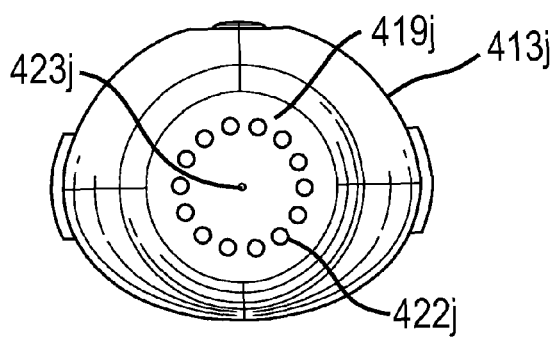
Figure 11K:
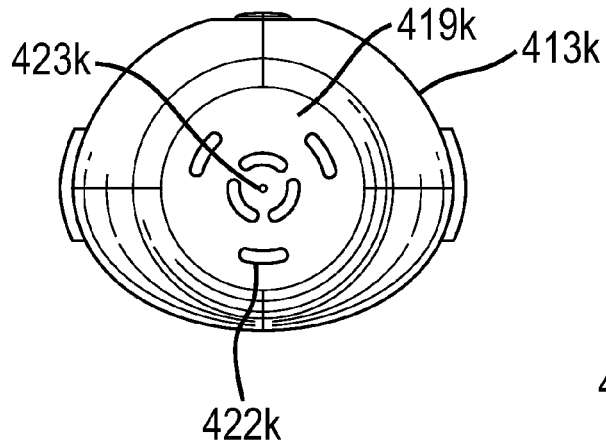
Figure 11L:
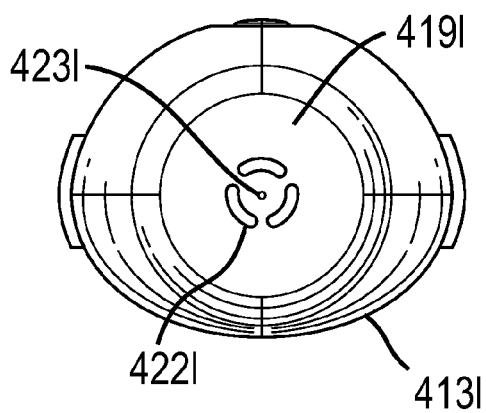
Figure 11M:
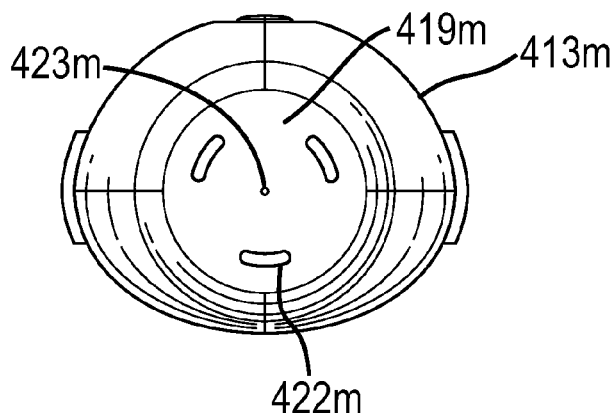
Figure 11N:
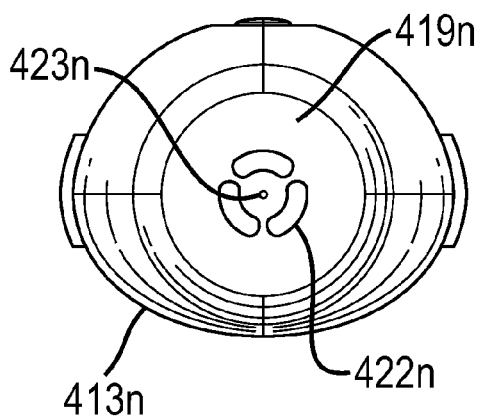

FIGS. 11a to 11n show other mouthpiece forms 413a to 413n, which may be employed in the drug dispenser device of FIGS. 7 to 9 and FIG. 10 as an alternative to the mouthpieces 13, 113 thereof. These alternative mouthpiece forms 413a to 413n differ only in the size, shape and number of respective air holes 422a to 422n provided to the rear of the internal section 419a to 419n of these alternative mouthpiece forms 413a to 413n, which air holes 422a to 422n are as before, arranged about a spray orifice 423a to 423n.

Thus, FIGS. 11a to 11d and 11i show different arrangements of four circular air holes 422a to 422d and 422i; FIGS. 11e and 11f show different arrangements of three slot-like air holes 422e, 422f; FIGS. 11g and 11h show different arrangements of six slot-like air holes 422g, 422h; FIG. 11j shows an arrangement of many circular air holes 422j; FIG. 11k shows an arrangement of six curved slot air holes 422k arranged in two concentric rings; FIGS. 11l to 11n show different arrangements of three curved slot air holes 422l to 422n arranged in a ring pattern.

The form of the outlet (e.g. mouthpiece) as shown herein assists with ease of maintaining the cleanliness thereof. In particular, the annular air flow provided at the inner peripheral surface of the outlet of particular embodiments herein assists in maintaining surface cleanliness thereof.

Each of the above-described embodiments of the present invention may be modified to incorporate one or more features disclosed in any of the US provisional applications and/or International (PCT) applications referred to in the 'Cross-Reference to Related Applications' section supra or in any of the other patents/patent applications referred to herein. The embodiments may further be modified to incorporate one or more features in the statements of invention and appended claims.

The actuator and/or inhaler herein are suitable for use in the dispensing of a drug formulation to a patient. The drug formulation may take any suitable form and include other suitable ingredients such as diluents, solvents, carriers and propellants.

Administration of drug may be indicated for the treatment of mild, moderate or severe acute or chronic symptoms or for prophylactic treatment. It will be appreciated that the precise dose administered will depend on the age and condition of the patient, the particular drug used and the frequency of administration and will ultimately be at the discretion of the attendant physician. Embodiments are envisaged in which combinations of drugs are employed.

Appropriate drugs may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), salmefamol, carbuterol, mabuterol, etanterol, naminterol, clenbuterol, flerbuterol, bambuterol, indacaterol, formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α$_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the drugs may be used in the form of salts, (e.g., as alkali metal or amine salts or as acid addition salts) or as esters (e.g., lower alkyl esters) or as solvates (e.g., hydrates) to optimise the activity and/or stability of the drug.

The drug formulation may in embodiments, be a monotherapy (i.e. single active drug containing) product or it may be a combination therapy (i.e. plural active drugs containing) product.

Suitable drugs or drug components of a combination therapy product are typically selected from the group consisting of anti-inflammatory agents (for example a corticosteroid or an NSAID), anticholinergic agents (for example, an M$_1$, M$_2$, M$_1$/M$_2$ or M$_3$ receptor antagonist), other β$_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester and 9α,21 dichloro-11β,17α methyl-1,4 pregnadiene 3,20 dione-17-[2'] furoate (mometasone furoate).

Further corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful are disclosed WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists), inhibitors of cytokine synthesis or 5-lipoxygenase inhibitors. Examples of iNOS inhibitors include those disclosed in WO93/13055, WO98/30537, WO02/50021, WO95/34534 and WO99/62875. Examples of CCR3 inhibitors include those disclosed in WO02/26722.

Suitable bronchodilators are β$_2$-adrenoreceptor agonists, including salmeterol (which may be a racemate or a single enantiomer, such as the R-enantiomer), for instance salmeterol xinafoate, salbutamol (which may be a racemate or a single enantiomer, such as the R-enantiomer), for instance salbutamol sulphate or as the free base, formoterol (which may be a racemate or a single diastereomer, such as the R,R-diastereomer), for instance formoterol fumarate or terbutaline and salts thereof. Other suitable β$_2$-adrenoreceptor agonists are 3-(4-{[6-({(2R)-2-hydroxy-2-[4-hydroxy-3-(hydroxymethyl)phenyl]ethyl}amino)hexyl]oxy}butyl)benzenesulfonamide, 3-(3-{[7-({(2R)-2-hydroxy-2-[4-hydroxy-3-hydroxymethyl)phenyl]ethyl}-amino)heptyl]oxy}propyl)benzenesulfonamide, 4-{(1R)-2-[(6-{2-[(2,6-dichlorobenzyl)oxy]ethoxy}hexyl)amino]-1-hydroxyethyl}-2-(hydroxymethyl)phenol, 4-{(1R)-2-[(6-{4-[3-(cyclopentylsulfonyl)phenyl]butoxy}hexyl)amino]-1-hydroxyethyl}-2-(hydroxymethyl)phenol, N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, and N-2{2-[4-(3-phenyl-4-methoxyphenyl)aminophenyl]ethyl}-2-hydroxy-2-(8-hydroxy-2(1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one. Preferably, the β$_2$-adrenoreceptor agonist is a long acting β$_2$-adrenoreceptor agonist (LABA), for example a compound which provides effective bronchodilation for about 12 hours or longer.

Other β$_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Preferred phosphodiesterase 4 (PDE4) inhibitors are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol].

Other suitable drug compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in WO04/024728, WO04/056823 and WO04/103998, all of Glaxo Group Limited.

Suitable anticholinergic agents are those compounds that act as antagonists at the muscarinic receptor, in particular those compounds, which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds include the alkaloids of the belladonna plants as illustrated by the likes of atropine, scopolamine, homatropine, hyoscyamine; these compounds are normally administered as a salt, being tertiary amines.

Other suitable anti-cholinergics are muscarinic antagonists, such as (3-endo)-3-(2,2-di-2-thienylethenyl)-8,8-dimethyl-8-azoniabicyclo[3.2.1]octane iodide, (3-endo)-3-(2-cyano-2,2-diphenylethyl)-8,8-dimethyl-8-azoniabicyclo[3.2.1]octane bromide, 4-[hydroxy(diphenyl)methyl]-1-{2-[(phenylmethyl)oxy]ethyl}-1-azonia bicyclo[2.2.2]octane bromide, (1R,5S)-3-(2-cyano-2,2-diphenylethyl)-8-methyl-8-{2-[(phenylmethyl)oxy]ethyl}-8-azoniabicyclo[3.2.1]octane bromide, (endo)-3-(2-methoxy-2,2-di-thiophen-2-yl-ethyl)-8,8-dimethyl-8-azonia-bicyclo[3.2.1]octane iodide, (endo)-3-(2-cyano-2,2-diphenyl-ethyl)-8,8-dimethyl-8-azonia-bicyclo[3.2.1]octane iodide, (endo)-3-(2-carbamoyl-2,2-diphenyl-ethyl)-8,8-dimethyl-8-azonia-bicyclo[3.2.1]octane iodide, (endo)-3-(2-cyano-2,2-di-thiophen-2-yl-ethyl)-8,8-dimethyl-8-azonia-bicyclo[3.2.1]octane iodide, and (endo)-3-{2,2-diphenyl-3-[(1-phenyl-methanoyl)-amino]-propyl}-8,8-dimethyl-8-azonia-bicyclo[3.2.1]octane bromide.

Particularly suitable anticholinergics include ipratropium (e.g. as the bromide, sold under the name Atrovent), oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118. Also of interest are revatropate (for example, as the hydrobromide, CAS 262586-79-8) and LAS-3.4273 which is disclosed in WO01/04118, darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds disclosed in U.S. Ser. No. 60/487,981 and U.S. Ser. No. 60/511,009.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine.

Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Exemplary H1 antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

The drug, or one of the drugs, may be an H3 antagonist (and/or inverse agonist). Examples of H3 antagonists include, for example, those compounds disclosed in WO2004/035556 and in WO2006/045416.

Other histamine receptor antagonists which may be used include antagonists (and/or inverse agonists) of the H4 receptor, for example, the compounds disclosed in Jablonowski et al., *J. Med. Chem.* 46:3957-3960 (2003).

In embodiments, the drug formulation includes one or more of a $\beta_2$-adrenoreceptor agonist, a corticosteroid, a PDE-4 inhibitor and an anti-cholinergic.

Generally, powdered drug particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat.

The amount of any particular drug or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The drugs for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1.5 mg per day.

In one embodiment, the drug is formulated as any suitable aerosol formulation, optionally containing other pharmaceutically acceptable additive components. In embodiments, the aerosol formulation comprises a suspension of a drug in a propellant. In embodiments, the propellant is a fluorocarbon or hydrogen-containing chlorofluorocarbon propellant.

Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above-identified compounds or mixtures, preferably binary mixtures, with other fluorocarbons or hydrogen-containing chloro-fluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof.

The drug formulations are preferably substantially free of chlorofluorocarbons such as $CCl_3F$, $CCl_2F_2$ and $CF_3CCl_3$. Preferably, the propellant is liquefied HFA134a or HFA-227 or mixtures thereof.

The propellant may additionally contain a volatile adjuvant such as a saturated hydrocarbon for example propane, n-butane, liquefied, pentane and isopentane or a dialkyl ether for example dimethyl ether. In general, up to 50% w/w of the propellant may comprise a volatile hydrocarbon, for example 1 to 30% w/w. However, formulations, which are free or substantially free of volatile adjuvants are preferred. In certain cases, it may be desirable to include appropriate amounts of water, which can be advantageous in modifying the dielectric properties of the propellant.

A polar co-solvent such as $C_{2-6}$ aliphatic alcohols and polyols e.g. ethanol, isopropanol and propylene glycol, preferably ethanol, may be included in the drug formulation in the desired amount to improve the dispersion of the formulation, either as the only excipient or in addition to other excipients such as surfactants. In embodiments, the drug formulation may contain 0.01 to 5% w/w based on the propellant of a polar co-solvent e.g. ethanol, preferably 0.1 to 5% w/w e.g. about 0.1 to 1% w/w. In embodiments herein, the solvent is added in sufficient quantities to solubilise part or all of the drug component, such formulations being commonly referred to as 'solution' aerosol drug formulations.

A surfactant may also be employed in the aerosol formulation. Examples of conventional surfactants are disclosed in EP-A-372,777. The amount of surfactant employed is desirable in the range 0.0001% to 50% weight to weight ratio relative to the drug, in particular, 0.05 to 10% weight to weight ratio.

The aerosol drug formulation desirably contains 0.005-10% w/w, preferably 0.005 to 5% w/w, especially 0.01 to 2% w/w, of drug relative to the total weight of the formulation.

In another embodiment, the drug is formulated as any suitable fluid formulation, particularly a solution (e.g. aqueous) formulation or a suspension formulation, optionally containing other pharmaceutically acceptable additive components.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Suitable solution formulations may comprise a solubilising agent such as a surfactant. Suitable surfactants include α-[4-(1,1,3,3-tetramethylbutyl)phenyl]-ω-hydroxypoly (oxy-1,2-ethanediyl)polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (e.g. PEG 200) and propylene glycol; sugars such as dextrose; and ethanol. Dextrose and polyethylene glycol (e.g. PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (e.g. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate drug and optionally suspending agents, preservatives, wetting agents or isotonicity adjusting agents.

Suitable suspending agents include carboxymethylcellulose, veegum, tragacanth, bentonite, methylcellulose and polyethylene glycols.

Suitable wetting agents function to wet the particles of drug to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The drug dispenser device herein is in one embodiment suitable for dispensing aerosolized drug (e.g. for inhalation via the mouth) for the treatment of respiratory disorders such as disorders of the lungs and bronchial tracts including asthma and chronic obstructive pulmonary disorder (COPD). In another embodiment, the invention is suitable for dispensing aerosolized drug (e.g. for inhalation via the mouth) for the treatment of a condition requiring treatment by the systemic circulation of drug, for example migraine, diabetes, pain relief e.g. inhaled morphine.

Administration of drug in aerosolized form may be indicated for the treatment of mild, moderate or severe acute or chronic symptoms or for prophylactic treatment. It will be appreciated that the precise dose administered will depend on the age and condition of the patient, the particular particulate drug used and the frequency of administration and will ultimately be at the discretion of the attendant physician. When combinations of drugs are employed the dose of each component of the combination will in general be that employed for each component when used alone. Typically, administration may be one or more times, for example from 1 to 8 times per day, giving for example 1, 2, 3 or 4 aerosol puffs each time. Each valve actuation, for example, may deliver 5 μg, 100 μg, 200 μg or 250 μg of a drug. Typically, each filled canister for use in a metered dose inhaler contains 60, 100, 120 or 200 metered doses or puffs of drug; the dosage of each drug is either known or readily ascertainable by those skilled in the art.

In another embodiment, the drug dispenser device herein is suitable for dispensing fluid drug formulations for the treatment of inflammatory and/or allergic conditions of the nasal passages such as rhinitis e.g. seasonal and perennial rhinitis as well as other local inflammatory conditions such as asthma, COPD and dermatitis. A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 μg, 50 μg, 100 μg, 200 μg or 250 μg of active drug. The precise dosage is either known or readily ascertainable by those skilled in the art.

It will be understood that the present invention has been described above by way of example only and that the above description can be modified in many different ways without departing from the scope of the invention as defined by the appended claims.

It will be further understood that the inclusion of reference numerals in the claims is for illustrative purposes only, and not meant to have, nor to be taken as having, a limiting effect on the scope of the claims.

All publications, patents, and patent applications cited herein are hereby incorporated herein by reference to their entirety to the same extent as if each publication, patent, or patent application was specifically and individually indicated to be incorporated by reference.

It must be noted that, as used in the specification and appended claims, the singular forms "a", "an", "the" and "one" include plural referents unless the content clearly dictates otherwise.

What is claimed is:

1. An actuator for an inhaler for delivering drug by inhalation, comprising:
a housing for receiving a canister which comprises a body which includes a base and a head and defines a chamber for containing drug, and a valve stem which extends from the body and from which drug is in use delivered on actuation of the canister;
an outlet through which a user in use inhales; and
a nozzle assembly which provides for delivery of drug through the outlet, wherein the nozzle assembly comprises a nozzle block in contact with the valve stem of the canister and, a nozzle outlet which is fluidly connected to the nozzle block and includes an outlet orifice from which drug is in use delivered, wherein the nozzle outlet is integrally formed with the outlet as a separate component to the nozzle block, and wherein the outlet includes a plurality of air flow paths which together provide for a substantially annular air flow at an inner peripheral surface of the outlet on inhalation by the user through the outlet, such as to provide a sheathing air flow to an aerosol spray when delivered from the nozzle outlet.

2. The actuator of claim 1, wherein the nozzle block is coupled to the housing.

3. The actuator of claim 2, wherein the nozzle block is integrally formed with the housing.

4. The actuator of claim 1, wherein the outlet is formed separately of the housing.

5. The actuator of claim 1, wherein the outlet is integrally formed with the housing.

6. The actuator of claim 1, wherein the nozzle block includes a laterally-directed cavity which receives the nozzle outlet.

7. The actuator of claim 6, wherein the nozzle outlet is captively disposed in the laterally-directed cavity.

8. The actuator of claim 7, wherein the nozzle outlet is a snap-fit in the laterally-directed cavity.

9. The actuator of claim 7, wherein the laterally-directed cavity includes a recess and the nozzle outlet includes a projection which is captively engaged in the recess or vice-versa.

10. The actuator of claim 7, wherein the nozzle outlet is an interference fit in the laterally-directed cavity.

11. The actuator of claim 1, wherein the annular air flow is in a direction away from the nozzle outlet.

12. The actuator of claim 1, wherein the outlet has a closed rear section which partitions the outlet from the housing, such that, on inhalation through the outlet, an air flow is drawn only from an outer peripheral surface of the outlet.

13. The actuator of claim 12, wherein the rear section of the outlet has an arcuate shape.

14. The actuator of claim 13, wherein the rear section of the outlet has an elliptical shape.

15. The actuator of claim 12, wherein the outlet comprises an external section which is configured to be gripped in the lips of the user and defines an open end through which drug is in use delivered and an internal section which defines the rear section to which the nozzle outlet is coupled.

16. The actuator of claim 1, wherein nozzle outlet includes a delivery channel which is fluidly connected to the outlet orifice and narrows towards the same.

17. The actuator of claim 16, wherein the delivery channel has arcuate wall sections.

18. The actuator of claim 16, wherein the delivery channel has substantially straight wall sections.

19. The actuator of claim 1, wherein the outlet orifice is a spray orifice which provides for delivery of an aerosol spray of drug.

20. The actuator of claim 1, wherein the outlet is a mouthpiece.

21. The actuator of claim 1 wherein the at least one air flow path which provides for a substantially annular air flow at an inner peripheral surface of the outlet is enabled by the provision of one or more air inlets to the nozzle outlet.

22. The actuator of claim 21, wherein the nozzle outlet is integrally formed with the outlet.

23. The actuator of claim 21, wherein from 3 to 20 air inlets are provided to the nozzle outlet.

24. The actuator of claim 21, wherein the combined cross-sectional area of the one or more air inlets is from 10 to 100 $mm^2$.

25. The actuator of claim 21, wherein the one or more air inlets are selected from the group consisting of circular form cross-section, oval form cross-section, wedge form cross-section or slot form cross-section.

26. The actuator of claim 21, wherein the nozzle outlet is essentially bucket-shaped and the outlet orifice and one or more air inlets are provided to the bucket base thereof.

27. The actuator of claim 26, wherein the one or more air inlets are arranged about the outlet orifice.

28. The actuator of claim 27 wherein, the one or more air inlets adopt a symmetric arrangement about the outlet orifice.

29. The actuator of claim 27, wherein the one or more air inlets adopt a radial arrangement about the outlet orifice.

30. The actuator of claim 29, wherein the one or more air inlets adopt a circular arrangement about the outlet orifice.

31. The actuator of either of claim 29, wherein the one or more air inlets adopt a radiating out arrangement about the outlet orifice.

32. An inhaler comprising the actuator of claim 1 and a canister containing drug.

33. A kit of parts comprising the actuator of claim 1 and a canister containing drug.

* * * * *